United States Patent
Von Knebel-Döberitz et al.

[11] Patent Number: 6,027,891
[45] Date of Patent: Feb. 22, 2000

[54] METHOD OF EARLY DETECTION OF HPV-ASSOCIATED CARCINOMAS AND EXTREME DYSPLASIAS CAUSED BY HPV

[75] Inventors: Magnus Von Knebel-Döberitz; Stefan Wörner; Florian Emmerich, all of Heidelberg, Germany

[73] Assignee: Deutsches Krebsforschungszentrum des Offentlichen Rechts, Heidelberg, Germany

[21] Appl. No.: 08/913,547

[22] PCT Filed: Feb. 23, 1996

[86] PCT No.: PCT/DE96/00306

§ 371 Date: Jan. 28, 1998

§ 102(e) Date: Jan. 28, 1998

[87] PCT Pub. No.: WO96/26293

PCT Pub. Date: Aug. 29, 1996

[30] Foreign Application Priority Data

Feb. 24, 1995 [DE] Germany ............ 195 06 561

[51] Int. Cl.$^7$ .................................................. C12Q 1/68
[52] U.S. Cl. ............................ 435/6; 435/5; 935/19
[58] Field of Search ........................ 435/6, 5; 935/19

[56] References Cited

U.S. PATENT DOCUMENTS 5,821,048 10/1998 Howley .......................... 435/5

FOREIGN PATENT DOCUMENTS

| 0 373 352 A2 | 6/1990 | European Pat. Off. . |
| 0 402 132 A2 | 12/1990 | European Pat. Off. . |
| 0 466 367 A1 | 1/1992 | European Pat. Off. . |
| WO 88/06634 | 9/1988 | WIPO . |
| WO 91/08312 | 6/1991 | WIPO . |
| WO 94/26934 | 11/1994 | WIPO . |

OTHER PUBLICATIONS

Cornelissen, et al., "Uniformity of the Splicing Pattern of the E6/E7 Transcripts in Human Papillomarvirus type 16–Transformed Human Fibroblasts, Human Cervical Premalignant Lesions and Carcinomas", *Journal of General Virology*—71:1243–1246 (1990).

Primary Examiner—Kenneth R. Horlick
Assistant Examiner—Janell E. Taylor
Attorney, Agent, or Firm—Albert P. Halluin; J. David Smith; Howrey & Simon

[57] ABSTRACT

This invention relates to a method of detection of an mRNA having HPV and cellular sequences in a body sample, comprising the following steps:

(a) obtaining a body sample;
(b) isolating mRNA from the body sample of (a);
(c) translating the mRNA of (b) into cDNA using a primer common for reverse transcription;
(d) amplifying the cDNA of (c) by a PCR reaction with a 5' HPV primer and a 3' primer having sequences of the primer of (c);
(e) cleaving the amplified cDNA of (d) with an endonuclease cleaving on the 5' side of the HPV polyadenylation sequence;
(f) amplifying the non-cleaved cDNA of (e) with the primers of (d) or with "nested" primers; and
(g) detecting the amplified cDNA of (f).

Furthermore, this invention concerns the use of such a method of early detection of HPV-associated carcinomas and extreme dysplasias caused by HPV, respectively.

7 Claims, 1 Drawing Sheet

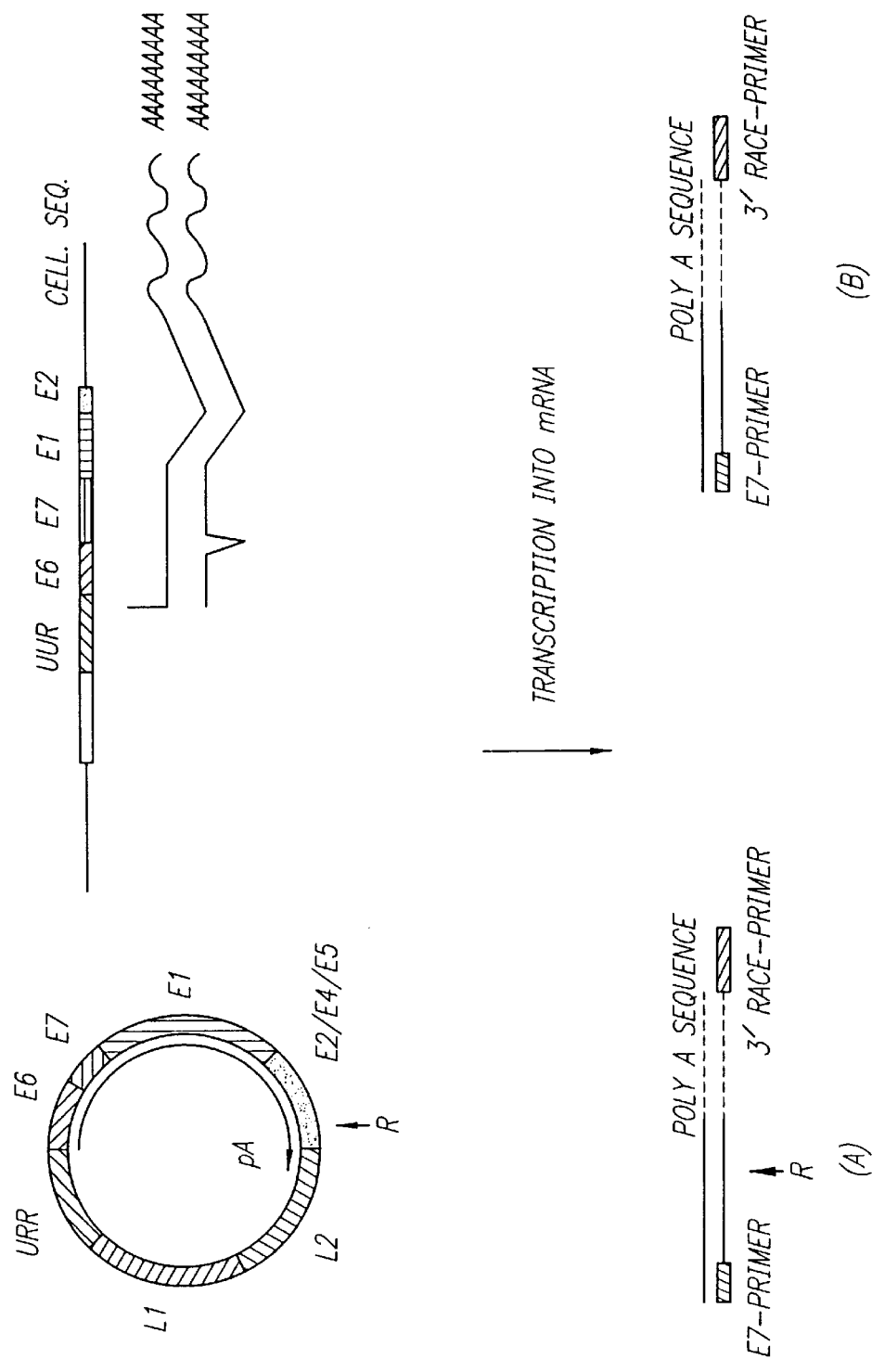

METHOD OF EARLY DETECTION OF HPV-ASSOCIATED CARCINOMAS AND EXTREME DYSPLASIAS CAUSED BY HPV

The present application is a U.S. nationalization pursuant to 35 U.S.C. 371 of PCT/DE96/00306 filed on Feb. 23, 1996 which is in turn based on German Patent Application No. 195 06 561.1 filed on February 24, 1995.

The present invention relates to a method for early detection of HPV-associated carcinomas and extreme dysplasias caused by HPV.

It is known that many people suffer from persisting infections caused by human papilloma viruses (referred to as HPVs below). Furthermore, it is known that over 95% of all anogenital carcinomas, particularly the cervical carcinoma of the uterus, and a considerable percentage of carcinomas in the oropharynx are associated with persisting infections caused by what are called "high-risk types" of the HPVs.

Therefore, in the cancer screening of women smears of the cervix uteri are examined as to changes in the cells, which are caused by persisting infections caused by HPVs. Such changes are divided into differing degrees of severity. If dysplastic cells are detected, the lesion will usually be removed by conization of the cervix uteri. Since this method has been carried out regularly for the early detection of carcinomas, the incidence of invasive cervical carcinoma has decreased considerably.

Nevertheless, the above method includes considerable drawbacks which include, for example: (1) The evaluation of the cell picture is subject to subjective influences which are due to a cytologist and, depending on his experience; may lead to wrong positive or wrong negative results. (2) By the cytologic evaluation it is not possible to make a distinction between lesions which may regress spontaneously and lesions which may change to an invasive carcinoma. Up to 80% of the early lesions regress spontaneously. However, for reasons of safety these lesions are still removed by conization to avoid the risk of a possible malignancy. The conization per se also results in a certain morbidity, i.e. cervical insufficiency, and obstetric complications connected therewith. (3) The cytologic examination is not sensitive enough in some cases, so that in spite of regular cytologic controls, invasive carcinomas are overlooked in some cases.

Recent studies refer to the fact that for the formation of carcinomas and extreme dysplasias, respectively, an uncontrolled expression of HPV genes, particularly genes E6 and E7, is necessary in the case of cells having a persisting infection caused by HPVs. Reference is also made to the fact that in HPV-associated carcinomas, HPV genomes or at least genes E6 and E7 are integrated into the cell DNA and expressed together with cellular sequences.

This could mean that for the uncontrolled expression of the above genes, they have to be expressed together with cellular sequences. Such an expression product could then be suited to indicate at an early stage the formation of HPV-associated carcinomas and extreme dysplasias caused by HPV, respectively.

The applicant investigated the above and found that the addressed expression product stands for the uncontrolled expression of the genes and is thus suitable for the early detection of HPV-associated carcinomas and extreme dysplasias caused by HPV, respectively. It proved to be favorable to detect the expression product in the form of an mRNA having HPV and cellular sequences. A method suited for this purpose comprises the following steps:

(a) obtaining of a body sample, (b) isolating mRNA from the body sample of (a), (c) translating the mRNA of (b) into cDNA using a primer common for reverse transcription, (d) amplifying the cDNA of (c) by a PCR reaction with an HPV primer (5' primer) and a primer (3' primer) having sequences of the primer of (c), (e) cleaving the amplified cDNA of (d) with an endonuclease cleaving on the 5' side of the HPV polyadenylation sequence, (f) amplifying the non-cleaved cDNA of (e) with the primers of (d) or with "nested" primers, and (g) detecting the amplified cDNA of (f).

A body sample in which an mRNA having HPV and cellular sequences may be detected, is taken from a patient. Samples suitable for this purpose are inter alia a smear or surface biopsy, an organ punctate and a biopsy, respectively, blood, sputum, urine, stool, liquor, bile, lymph and a gastrointestinal secretion. A smear or surface biopsy is preferred.

The body sample, preferably a smear or surface biopsy, is taken and prepared as usual. The mRNA is isolated from the body sample according to common methods. It is favorable to use a purchasable extraction kit, e.g. GlassMax, Gibco BRL. Contaminating DNA in the mRNA preparation is removed by common DNase digestion.

The resulting mRNA is subjected to reverse transcription, a common primer being used. The primer includes preferably one of the following sequences:

5'-GAC TCG AGT CGA CAT CGA TTT TTT TTT TTT TTT TT-3' SEQ ID NO:1;

5'-GAC TCG AGT CGA CAT CGA GAC GTC GGA GTG CGA GCA TCG ATT TTT TTT TTT TTT TTT-3' SEQ ID NO:2.

For reverse transcription it is possible to use a common reverse transcriptase, preferably an MMLV-reverse transcriptase (e.g. superscript II, Gibco BRL). A preferred reaction batch comprises the following:

4 μl 5×reaction buffer

2 μl 0.1 M DTT

1 μl 10 mM dNTPs 1 ml 25 pmoles/μl primer 200 units of reverse transcriptase about 1 μg RNA Batch ad 20 μl, reaction conditions:

10 min, 70° C.; 60 min, 42° C.; 30 min, 52° C.

The resulting cDNA is subjected to a polymerase chain reaction (PCR reaction). It is favorable to use a purchasable Taq polymerase (e.g. Gibco BRL). An HPV primer (5' primer), preferably from the E6–E7 region, and a primer (3' primer) which has sequences, preferably from the 5' region, of the primer used above for reverse transcription are used as primers.

The primers of the following sequences are especially suitable as 5' primers for the E6–E7 region of frequently occurring high-risk HPV types:

```
HPV 16:  5'- CGG ACA GAG CCC ATT ACA AT - 3'        nt 701-nt 720 SEQ ID NO:3

HPV 18:  5'- TAG AAA GCT CAG CAG ACG ACC - 3'       nt 816-nt 836 SEQ ID NO:4

HPV 31:  5'- TAT GAG CAA TTA TTA CCC GAC AGC - 3'   nt 632-nt 642 SEQ ID NO:5

HPV 33:  5'- TTT ATA TCC TGA ACC AAC TGA            nt 614-nt 642 SEQ ID NO:6
             CCT ATA CT - 3'

HPV 35:  5'- TAG ATT TGG AAC CCG AGG C - 3'         nt 599-nt 681 SEQ ID NO:7

HPV 39:  5'- TCA CGA GCA ATT AGG AGA GTC A - 3'     nt 599-nt 681 SEQ ID NO:8

HPV 52:  5'- GCA ACC TGA AAC AAC TGA CCT AC - 3'    nt 597-nt 608 SEQ ID NO:9
```

The primer of the following sequence is particularly suitable as a 3' primer:

5'-GAC TCG AGT CGA CAT CG-3' SEQ ID NO:10.

According to the invention one or more 5' primers and/or 3' primers can be used in the PCR reaction. If several 5' primers are present, they may be for an HPV type or for several HPV types.

The PCR reaction is carried out under standard conditions. These are e.g. the following conditions:

10 µl 10×Taq polymerase buffer

10 µl 2 mM dNTPs

3 µl 50 mM MgCl$_2$

1 µl 25 pmoles/µl 5' primer

1 µl 25 pmoles/µl 3' primer 1 unit of Taq DNA polymerase

2 µl cDNA (from reverse transcription)

ad 100 µl

Reaction temperatures: 1.5 min, 93° C.; 30 sec, 93° C.; 30 sec, x° C. (x=differing annealing temperature depending on the primer), 2 min, 72° C., repeated in 30 cycles; final elongation 6 min, 72° C. The annealing temperatures are chosen corresponding to the thermodynamics of the primers used. This is a common step for a person skilled in the art.

For controlling the above enrichment of mRNA and its translation into cDNA, it is recommended to carry out a GAPDH PCR reaction. It is made under the above conditions. The primers used are, e.g.:

GAPDH (forward): 5'-CAT CTC TGC CCC CTC TGC GA-3' SEQ ID NO:11

GAPDH (reverse): 5'-GGA TGA CCT TGC CCA CAG CCT-3' SEQ ID NO:12.

Amplified GAPDH sequences are detected as usual, e.g. by Southern blot hybridization using a labeled oligonucleotide specific for GAPDH. This oligonucleotide may have e.g. the following sequence:

5'-CTC TCC AGA ACA TCA TCC CTG-3' SEQ ID NO:13.

Above reactions which do not relate to the control serve for obtaining cDNAs which originate from mRNAs including HPV-E6-E7 and polyadenylation sequences. Such mRNAs may originate from episomal HPVs present in cells having a persisting HPV infection. The mRNAs may also originate from HPVs integrated into the cell DNA and have cellular sequences. For the detection of the latter mRNAs, the above cDNAs are cleaved with a restriction enzyme cleaving on the 5' side of the HPV-polyadenylation sequence. Thus, only those cDNAs are cleaved which are obtained from episomal HPVs. The other cDNAs obtained from integrated HPVs are not cleaved, since they are lacking the restriction site for the restriction enzyme. This is due to the recombination between viral and cellular sequences, by which sequences on the 5' side of the HPV-polyadenylation sequence are not co-transcribed (cf. fig.).

The following restriction enzymes are especially suitable as restriction enzymes for the above high-risk HPV types:

| HPV 16 | Alw NI  |
|--------|---------|
| HPV 18 | Nde I   |
| HPV 31 | BsmBI   |
| HPV 33 | Sca I   |
| HPV 39 | Hph I   |
| HPV 52 | BstE II |

The non-cleaved cDNAs are subjected to another PCR reaction. For this purpose, it is possible to use the primers which were employed above for the first PCR reaction.

It is also favorable to employ "nested primers" which confine the cDNAs to be amplified. Such primers may be used as both 5' primers and 3' primers. Combinations of primers which were used for the first PCR reaction and "nested" primers may also be favorable.

The primers of the following sequences are especially suitable as "nested" 5' primers for the E6–E7 region of the above high-risk HPV types:

```
HPV 16:  5'- CCT TTT GTT GCA AGT GTG ACT SEQ ID NO:14  nt 728-nt 753
             CTA CG - 3'

HPV 18:  5'- GAG CAT CCA GCA GCT GTT TC  SEQ ID NO:15  nt 840-nt 864
             TGA A - 3'

HPV 31:  5'- CAC GAG CAC ACA AGT AGA TAT SEQ ID NO:16  nt 766-nt 798
             TCG CAT ATT GCA - 3'
```

-continued

```
HPV 33:  5'- TCA ACA GTA CAG CAA GTG ACC  SEQ ID NO: 17  nt 778-nt 807
             TAC GAA CCA - 3'

HPV 35:  5'- AGA GGA GGA GGA AGA TAC TAT  SEQ ID NO: 18  nt 657-nt 687
             TGA CGG TCC A - 3'

HPV 39:  5'- GTT AAT CAC CAA CAT CAA CTA  SEQ ID NO: 19  nt 727-nt 759
             CTA GCC AGA CGG -3'

HPV 52:  5'- CGG CCA GAT GGA CAA GCA GAA  SEQ ID NO: 20  nt 676-nt 698
             CA - 3'
```

The primer of the following sequence is especially suitable a nested 3' primer:

5'-GAC GTC GGA GTG CGA GCA TCG-3' SEQ ID NO:21.

The PCR reaction (second PCR reaction) is also carried out under standard conditions. These are e.g. the following conditions:

10 µl 10×Taq polymerase buffer
10 µl 2 mM dNTPs
3 µl 50 mM MgCl$_2$
1 µl 25 pmoles/µl 5' primer
1 µl 25 pmoles/µl 3' primer
1 unit Taq DNA polymerase
2 µl cDNA (from reverse transcription)
ad 100 µl Reaction temperatures: 1.5 min, 93° C.; 30 sec, 93° C.; 30 sec, x° C. (x=differing annealing temperature depending on the primer), 2 min, 72° C., repeated in 30 cycles; final elongation 6 min, 72° C. The annealing temperatures are chosen in accordance with the thermodynamics of the primers used. This is common practice for a person skilled in the art.

The amplified cDNAs are detected as usual, e.g. by Southern blot hybridization with labeled oligonucleotides specific for the individual HPV types. These may be e.g. the employed primers and "nested primers", respectively.

The method according to the invention distinguishes itself by a high degree of sensitivity and selectivity. It enables to tracking down very small amounts of HPV-infected cells which due to their genetic change would form HPV-associated carcinomas. The method according to the invention is therefore perfectly suited to be used for the early detection of HPV-associated carcinomas and extreme dysplasias caused by HPV, respectively.

BRIEF DESCRIPTION OF THE DRAWING

The FIGURE shows the identification of cDNAs which are obtained from episomal HPVs (a) and of cDNAs which are obtained from HPVs integrated into the cell DNA (b).

The present invention is explained by the following example.

Example: Detection of an mRNA Having HPV 18 and Cellular Sequences in a Smear mRNA was isolated by means of the purchasable extraction kit GlassMax from a patient's cervix uteri smear and enriched. The mRNA was subjected to reverse transcription, the primer used having the sequence 5'-GAC TCG AGT CGA CAT CGA TTT TTT TTT TTT TTT TT-3' SEQ ID NO:1.

The reaction batch was as follows:
4 µl 5×reaction buffer
2 µl 0.1 M DTT
1 µl 10 mM dNTPs
1 µl 25 pmoles/µl primer
200 units of reverse transcriptase of MMLV
about 1 µg of the above mRNA
Batch ad 20 µl Reaction conditions: 10 min 70° C.; 60 min, 42° C.; 30 min, 52° C.

The resulting cDNA was subjected to a PCR reaction. The 5' primer used was a primer suitable for HPV 18 and had the sequence 5'-TAG AAA GCT CAG CAG ACG ACC-3' SEQ ID NO:22. The 3' primer employed had the sequence 5'-GAC TCG AGT CGA CAT CG-3' SEQ ID NO: 23. The PCR reaction batch was as follows:

10 µl 10×Taq polymerase buffer
10 µl 2 mM dNTPs
3 µl 50 mM MgCl$_2$
1 µl 25 pmoles/µl 5' primer (HPV-18 primer)
1 µl 25 pmoles/µl 3' primer
1 unit Taq DNA polymerase
2 µl cDNA (from reverse transcription)
Batch ad 100 µl Reaction temperatures: 1.5 min, 93° C.; 30 sec, 93° C.; 30 sec, 56° C. (annealing temperature), 2 min, 72° C., repeated in 30 cycles; final elongation 6 min, 72° C.

For the purpose of control, the above cDNA was subjected to a GAPDH PCR reaction. It was carried out under the above conditions, the following were used as primers:

GAPDH (forward): 5'-CAT CTC TGC CCC CTC TGC TGA-3' SEQ ID NO: 11

GAPDH (reverse): 5'-GGA TGA CCT TGC CCA CAG CCT-3' SEQ ID NO:24

The amplified cDNA (control) was subjected to a Southern blot hybridization, a 32p-5'-labeled oligonucleotide including the sequence 5'-CTC TCC AGA ACA TCA TCC CTG-3' was used as sample. The hybridization temperature was about 50° C. below the melting temperature of the oligonucleotide.

An amplified DNA was detected.

The DNA amplified with the HPV 18 primer was subjected to a restriction cleavage with Nde I. The reaction batch was as follows:

1 µg DNA
2 µl 10×NdeI buffer
2 µl NdeI (10 U)
Batch ad 20 µl

Reaction conditions: 2 hours, 37° C.

The cleaved DNA was subjected to another PCR reaction under the following conditions:

10 μl 10×Taq polymerase buffer
10 μl 2 mM dNTPs
3 μl 50 mM MgCl$_2$
1 μl 25 pmoles/μl "nested" HPV 18 primer: 5'-GAG CAT TCC AGC AGC TGT TTC TGA A-3'
1 μl 25 pmoles/μl "nested" 3' primer: 5'-GAC GTC GGA GTG CGA GCA TCG-3'
1 unit Taq DNA polymerase
2 μl cDNA (from reverse transcription)
ad 100 μl Reaction temperatures: 1.5 min, 93° C.; 30 sec, 93° C.; 30 sec, 56° C. (annealing temperature), 2 min, 72° C., repeated in 30 cycles; final elongation 6 min, 72° C.

The amplified cDNA was subjected to Southern blot hybridization, a 32p-5'-labeled oligonucleotide having the sequence 5'-CAA TAC TGT CTT GCA ATA TAC-3' was used as sample. The hybridization temperature was about 5° C. below the melting point of the oligonucleotide.

An amplified cDNA was detected which was derived from an mRNA having HPV and cellular sequences.

We claim:

1. A method of detecting an mRNA having HPV and cellular sequences in a body sample, comprising the following steps:

(a) obtaining a body sample, (b) isolating mRNAs from the body sample of (a), (c) revurese transcribing the mRNAs of (b) into cDNAs using a common primer, (d) amplifying the cDNAs of (c) by a PCR reaction with a 5' HPV primer and a 3' primer having sequences of the primer of (c), (e) cleaving the amplified cDNAs of (d) with an endonuclease, wherein said endonuclease cleaves at a restriction site on the 5' side of an HPV-polyadenylation sequence, such that cDNAs obtained from episomal HPVs are cleaved and cDNAs obtained from integrated HPVs are not cleaved, (f) amplifying the non-cleaved cDNAs with the primers of (d) or with nested primers, and (g) detecting the amplified cDNAs of (f).

2. The method according to claim 1 wherein the body sample is selected from the group consisting of a smear, a surface biopsy, an organ punctate and a biopsy, blood, sputum, urine, stool, liquor, bile, lymph and a gastrointestinal secretion.

3. The method according claim 1 wherein the 5' primer is a 5' primer for high-risk HPV types.

4. The method according to claim 1 wherein more than one 5' primers or more than one 3' primers are used.

5. The method according to claim 1 wherein in step (d) at least one of the following is used as a 5' primer:

| | | |
|---|---|---|
| HPV 16: | 5'- CGG ACA GAG CCC ATT ACA AT - 3' | (SEQ. ID. NO: 3) |
| HPV 18: | 5'- TAG AAA GCT CAG CAG ACG ACC - 3' | (SEQ. ID. NO: 4) |
| HPV 31: | 5'- TAT GAG CAA TTA TTA CCC GAC AGC - 3' | (SEQ. ID. NO: 5) |
| HPV 33: | 5'- TTT ATA TCC TGA ACC AAC TGA CCT ATA CT - 3' | (SEQ. ID. NO: 6) |
| HPV 35: | 5'- TAG ATT TGG AAC CCG AGG C - 3' | (SEQ. ID. NO: 7) |
| HPV 39: | 5'- TCA CGA GCA ATT AGG AGA GTC A - 3' | (SEQ. ID. NO:8) |
| HPV 52: | 5'- GCA ACC TGA AAC AAC TGA CCT AC - 3' | (SEQ. ID. NO:9) |
| as 3'primer: | | |
| | 5'-GAC TGC AGT CGA CAT CG-3' | (SEQ. ID. NO: 10). |

6. The method according to claim 1 wherein in step (f) at least one of the following is used as a 5' primer:

```
HPV 16:  5'-CCT TTT GTT GCA AGT GTG ACT CTA CG-3'           (SEQ. ID. NO:14)

HPV 18:  5'-GAG CAT TCC AGC AGC TGT TTC TGA A-3'            (SEQ. ID. NO: 15)

HPV 31:  5'-CAC GAG CAC ACA AGT AGA TAT TCG CAT ATT GCA-3'  (SEQ. ID. NO: 16)

HPV 33:  5'-TCA ACA GTA CAG CAA GTG ACC TAC GAA CCA-3'      (SEQ. ID. NO: 17)

HPV 35:  5'-AGA GGA GGA GGA AGA TAC TAT TGA CGG TCC A-3'    (SEQ. ID. NO: 18)

HPV 39:  5'-GTT AAT CAC CAA CAT CAA CTA CTA GCC AGA CGG-3'  (SEQ. ID. NO: 19)

HPV 52:  5'-CGG CCA GAT GGA CAA GCA GAA CA-3'               (SEQ. ID. NO: 20);

and

5'-GAC GTC GGA GTG CGA GCA TCG-3'                  (SEQ. ID. NO: 21)

is used as a nested 3' primer.
```

7. A method for detecting HPV-associated carcinomas and extreme dysplasias caused by HPV comprising the steps of:

(a) obtaining a body sample, (b) isolating mRNAs from the body sample of (a), (c) reverese transcribing the mRNAs of (b) into cDNAs using a common primer, (d) amplifying the cDNAs of (c) by a PCR reaction with a 5' HPV primer and a 3' primer having sequences of the primer of (c), (e) cleaving the amplified cDNAs of (d) with an endonuclease, wherein said endonuclease cleaves at a restriction site on the 5' side of an HPV-polyadenylation sequence, such that cDNAs obtained from episomal HPVs are cleaved and cDNAs obtained from integrated HPVs are not cleaved, (f) amplifying the non-cleaved cDNAs with the primers of (d) or with nested primers, and (g) detecting the amplified cDNAs of (f).

* * * * *

```
                        SEQUENCE LISTING

<160> NUMBER OF SEQ ID NOS: 24

<210> SEQ ID NO 1
<211> LENGTH: 35
<212> TYPE: DNA
<213> ORGANISM: Homo sapiens

<400> SEQUENCE: 1
gactcgagtc gacatcgatt tttttttttt ttttt                               35

<210> SEQ ID NO 2
<211> LENGTH: 57
<212> TYPE: DNA
<213> ORGANISM: Homo sapiens

<400> SEQUENCE: 2
gactcgagtc gacatcgaga cgtcggagtg cgagcatcga tttttttttt ttttttt      57

<210> SEQ ID NO 3
<211> LENGTH: 20
<212> TYPE: DNA
<213> ORGANISM: Homo sapiens

<400> SEQUENCE: 3
cggacagagc ccattacaat                                                20

<210> SEQ ID NO 4
<211> LENGTH: 21
<212> TYPE: DNA
<213> ORGANISM: Homo sapiens

<400> SEQUENCE: 4
tagaaagctc agcagacgac c                                              21

<210> SEQ ID NO 5
<211> LENGTH: 21
<212> TYPE: DNA
<213> ORGANISM: Homo sapiens

<400> SEQUENCE: 5
tatgagcaat tacccgacag c                                              21

<210> SEQ ID NO 6
<211> LENGTH: 29
<212> TYPE: DNA
<213> ORGANISM: Homo sapiens
```

-continued

<400> SEQUENCE: 6
tttatatcct gaaccaactg acctatact                                29

<210> SEQ ID NO 7
<211> LENGTH: 19
<212> TYPE: DNA
<213> ORGANISM: Homo sapiens

<400> SEQUENCE: 7
tagatttgga acccgaggc                                           19

<210> SEQ ID NO 8
<211> LENGTH: 22
<212> TYPE: DNA
<213> ORGANISM: Homo sapiens

<400> SEQUENCE: 8
tcacgagcaa ttaggagagt ca                                       22

<210> SEQ ID NO 9
<211> LENGTH: 23
<212> TYPE: DNA
<213> ORGANISM: Homo sapiens

<400> SEQUENCE: 9
gcaacctgaa acaactgacc tac                                      23

<210> SEQ ID NO 10
<211> LENGTH: 17
<212> TYPE: DNA
<213> ORGANISM: Homo sapiens

<400> SEQUENCE: 10
gactcgagtc gacatcg                                             17

<210> SEQ ID NO 11
<211> LENGTH: 21
<212> TYPE: DNA
<213> ORGANISM: Homo sapiens

<400> SEQUENCE: 11
catctctgcc ccctctgctg a                                        21

<210> SEQ ID NO 12
<211> LENGTH: 21
<212> TYPE: DNA
<213> ORGANISM: Homo sapiens

<400> SEQUENCE: 12
ggatgacctt gcccacagcc t                                        21

<210> SEQ ID NO 13
<211> LENGTH: 21
<212> TYPE: DNA
<213> ORGANISM: Homo sapiens

<400> SEQUENCE: 13
ctctccagaa catcatccct g                                        21

-continued

```
<210> SEQ ID NO 14
<211> LENGTH: 26
<212> TYPE: DNA
<213> ORGANISM: Homo sapiens

<400> SEQUENCE: 14 cctttgttg caagtgtgac tctacg                                               26

<210> SEQ ID NO 15
<211> LENGTH: 25
<212> TYPE: DNA
<213> ORGANISM: Homo sapiens

<400> SEQUENCE: 15
gagcattcca gcagctgttt ctgaa                                                25

<210> SEQ ID NO 16
<211> LENGTH: 33
<212> TYPE: DNA
<213> ORGANISM: Homo sapiens

<400> SEQUENCE: 16
cacgagcaca caagtagata ttcgcatatt gca                                       33

<210> SEQ ID NO 17
<211> LENGTH: 30
<212> TYPE: DNA
<213> ORGANISM: Homo sapiens

<400> SEQUENCE: 17
tcaacagtac agcaagtgac ctacgaacca                                           30

<210> SEQ ID NO 18
<211> LENGTH: 31
<212> TYPE: DNA
<213> ORGANISM: Homo sapiens

<400> SEQUENCE: 18
agaggaggag gaagatacta ttgacggtcc a                                         31

<210> SEQ ID NO 19
<211> LENGTH: 33
<212> TYPE: DNA
<213> ORGANISM: Homo sapiens

<400> SEQUENCE: 19
gttaatcacc aacatcaact actagccaga cgg                                       33

<210> SEQ ID NO 20
<211> LENGTH: 23
<212> TYPE: DNA
<213> ORGANISM: Homo sapiens

<400> SEQUENCE: 20
cggccagatg gacaagcaga aca                                                  23

<210> SEQ ID NO 21
<211> LENGTH: 21
<212> TYPE: DNA
<213> ORGANISM: Homo sapiens
```

-continued

```
<400> SEQUENCE: 21
gacgtcggag tgcgagcatc g                                              21

<210> SEQ ID NO 22
<211> LENGTH: 21
<212> TYPE: DNA
<213> ORGANISM: Homo sapiens

<400> SEQUENCE: 22
tagaaagctc agcagacgac c                                              21

<210> SEQ ID NO 23
<211> LENGTH: 17
<212> TYPE: DNA
<213> ORGANISM: Homo sapiens

<400> SEQUENCE: 23
gactcgagtc gacatcg                                                   17

<210> SEQ ID NO 24
<211> LENGTH: 21
<212> TYPE: DNA
<213> ORGANISM: Homo sapiens

<400> SEQUENCE: 24
ggatgacctt gcccacagcc t                                              21
```